United States Patent
He et al.

(10) Patent No.: US 10,436,720 B2
(45) Date of Patent: Oct. 8, 2019

(54) ADAPTIVE AUTOMATIC DEFECT CLASSIFICATION

(71) Applicant: KLA-Tencor Corporation, Milpitas, CA (US)

(72) Inventors: Li He, San Jose, CA (US); Martin Plihal, Pleasanton, CA (US); Huajun Ying, San Jose, CA (US); Anadi Bhatia, Milpitas, CA (US); Amitoz Singh Dandiana, Chennai (IN); Ramakanth Ramini, Chennai (IN)

(73) Assignee: KLA-Tenfor Corp., Milpitas, CA (US)

( * ) Notice: Subject to any disclaimer, the term of this patent is extended or adjusted under 35 U.S.C. 154(b) by 391 days.

(21) Appl. No.: 14/991,901

(22) Filed: Jan. 8, 2016

(65) Prior Publication Data
US 2017/0082555 A1 Mar. 23, 2017

Related U.S. Application Data

(60) Provisional application No. 62/220,868, filed on Sep. 16, 2015, provisional application No. 62/274,013, (Continued)

(51) Int. Cl.
*G01N 21/95* (2006.01)
*G06N 20/00* (2019.01)
(Continued)

(52) U.S. Cl.
CPC ..... *G01N 21/9501* (2013.01); *G01N 21/8851* (2013.01); *G06N 20/00* (2019.01);
(Continued)

(58) Field of Classification Search
CPC ...... G06N 99/005; G06N 5/025; G06N 7/005; G06K 9/6256; G06K 9/6269
(Continued)

(56) References Cited

U.S. PATENT DOCUMENTS 5,966,459 A * 10/1999 Chen .................. G06K 9/00 348/126
5,978,497 A * 11/1999 Lee .................... G01N 15/1475 382/133

(Continued)

OTHER PUBLICATIONS

Zhou et al.—"Query Performance Prediction in Web Search Environments"—2007—https://dl.acm.org/citation.cfm?id=1277835 (Year: 2007).*

(Continued)

*Primary Examiner* — Scott A. Waldron
*Assistant Examiner* — Viker A Lamardo
(74) *Attorney, Agent, or Firm* — Ann Marie Mewherter

(57) ABSTRACT

Methods and systems for classifying defects detected on a specimen with an adaptive automatic defect classifier are provided. One method includes creating a defect classifier based on classifications received from a user for different groups of defects in first lot results and a training set of defects that includes all the defects in the first lot results. The first and additional lot results are combined to create cumulative lot results. Defects in the cumulative lot results are classified with the created defect classifier. If any of the defects are classified with a confidence below a threshold, the defect classifier is modified based on a modified training set that includes the low confidence classified defects and classifications for these defects received from a user. The modified defect classifier is then used to classify defects in additional cumulative lot results.

24 Claims, 7 Drawing Sheets

Related U.S. Application Data filed on Dec. 31, 2015, provisional application No. 62/387,461, filed on Dec. 23, 2015.

(51) Int. Cl.
*G01N 21/88* (2006.01)
*H01L 21/66* (2006.01)

(52) U.S. Cl.
CPC ............... *G01N 2021/8854* (2013.01); *G01N 2021/8883* (2013.01); *G01N 2201/06113* (2013.01); *G01N 2201/12* (2013.01); *H01L 22/12* (2013.01); *H01L 22/20* (2013.01)

(58) Field of Classification Search
USPC .......................................................... 706/12
See application file for complete search history.

(56) References Cited

U.S. PATENT DOCUMENTS

| | | | |
|---|---|---|---|
| 6,256,093 B1* | 7/2001 | Ravid | G01N 21/94 356/237.2 |
| 6,922,482 B1* | 7/2005 | Ben-Porath | G06K 9/6268 382/146 |
| 7,271,891 B1* | 9/2007 | Xiong | G01N 21/9501 250/559.39 |
| 7,991,217 B2* | 8/2011 | Nakagaki | G06K 9/6256 382/144 |
| 8,150,141 B2* | 4/2012 | Nakagaki | G06K 9/6256 382/144 |
| 8,437,534 B2* | 5/2013 | Shibuya | G01N 21/9501 382/149 |
| 8,452,076 B2* | 5/2013 | Nakagaki | G06K 9/6256 382/144 |
| 8,660,340 B2* | 2/2014 | Shibuya | G01N 21/9501 382/149 |
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 8,891,858 B1* | 11/2014 | Preetham | G06K 9/6256 382/159 |
| 2004/0156540 A1* | 8/2004 | Gao | G06K 9/6253 382/145 |
| 2005/0252752 A1* | 11/2005 | Fielden | G03F 7/70916 200/43.04 |
| 2006/0082763 A1 | 4/2006 | Teh et al. | |
| 2007/0201739 A1* | 8/2007 | Nakagaki | G06K 9/6256 382/149 |
| 2009/0297019 A1* | 12/2009 | Zafar | G03F 1/84 382/145 |
| 2011/0268345 A1* | 11/2011 | Nakagaki | G06K 9/6256 382/149 |
| 2011/0276935 A1* | 11/2011 | Fouquet | G06T 7/0006 716/112 |
| 2012/0029858 A1* | 2/2012 | Kulkarni | G05B 23/0297 702/108 |
| 2012/0128233 A1* | 5/2012 | Nakagaki | G06K 9/6256 382/149 |
| 2013/0279794 A1* | 10/2013 | Greenberg | G06T 7/001 382/149 |
| 2014/0071437 A1* | 3/2014 | Reich | G01J 1/4257 356/121 |
| 2014/0361159 A1* | 12/2014 | Pfaff | H01J 49/0036 250/282 |
| 2014/0362880 A1* | 12/2014 | Chuang | G02F 1/3558 372/22 |
| 2015/0098655 A1 | 4/2015 | Chang et al. | |
| 2015/0120639 A1* | 4/2015 | Shin | G06N 99/005 706/52 |
| 2015/0221076 A1 | 8/2015 | Gao et al. | |
| 2015/0262038 A1 | 9/2015 | Konuru et al. | |
| 2016/0170974 A1* | 6/2016 | Martinez Corria | G06F 17/289 704/4 |

OTHER PUBLICATIONS

Dougherty et al.—"Optimal robust classifiers"—2004—http://citeseerx.ist.psu.edu/viewdoc/download?doi=10.1.1.79.5794&rep=rep1&type=pdf (Year: 2004).*

Zhou et al.—"Ensembling Local Learners Through Multimodal Perturbation"—2005—https://ieeexplore.ieee.org/stamp/stamp.jsp?arnumber=1468246 (Year: 2005).*

Breiman, "Random Forests," Machine Learning, vol. 45, Issue 1, pp. 5-32 (2001).

International Search Report for PCT/US2016/052323 dated Dec. 23, 2016.

Written Opinion for PCT/US2016/052323 dated Dec. 23, 2016.

* cited by examiner

ADAPTIVE AUTOMATIC DEFECT CLASSIFICATION

BACKGROUND OF THE INVENTION

1. Field of the Invention

This invention generally relates to methods and systems for classifying defects on a specimen with an adaptive automatic defect classifier.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Once defects have been detected by inspection, additional information for the defects may be generated in one or more manners. For example, the defects may be re-visited by defect review in which a system having resolution capability greater than that used during inspection is used to generate images of the defects. Information about the defects generated using such images may then be used to determine a type (or classification) of the defects. For example, the defects may be classified as particle type defects, bridging type defects, scratch type defects, and the like. Although defect classifications may be determined based on information generated by defect review, sometimes, defect classification is performed based on information generated by inspection (e.g., if the information for the defect generated by inspection is adequate for defect classification and/or for preliminary classification based on the limited amount of information generated by inspection).

The methods, algorithms, and/or systems that perform classification of defects are often referred to as "defect classifiers." Defect classifier creation and monitoring typically includes three phases: a training phase, a validation phase, and a production phase. In the training phase, data may be collected until M lot results have been collected. An operator may then classify all the defects manually. Once M lot results have been collected, the classifier is created for classes that have more than N defects, where N is a pre-defined value. In the validation phase, data for M lots may be collected, and an operator classifies all the defects manually. If the accuracy of the validation lots is equal to or less than the training lots, the training classifier may be used for production. Otherwise, the validation classifier may be used for production. In the production phase, the contribution of the classifier may be monitored. An operator may classify the non-contribution bin (e.g., low confidence defects). If the confidence drops below a predefined threshold, the training phase may be performed again.

There are, however, a number of disadvantages to the currently performed methods for defect classifier creation and monitoring. For example, the classifier creation and monitoring process is cumbersome and cannot provide a relatively fast response to the dynamic defect changes in the fab. In addition, the user has to wait at least 2×M lots before the first classifier is created. Furthermore, during the training and validation phases, all the defects need to be manually classified and no assisted manual classification is provided. Moreover, if there is a defect shift or excursion, the user needs to wait at least M lots for the new classifier to be released to production. In addition, the training set may be severely imbalanced and not good enough to create a robust classifier. In many cases, the training set includes 90% nuisance and only 10% of the training set includes defects of interest (DOIs). Therefore, the number of defects is not sufficient to create a robust classifier. The currently used methods and systems also do not have a method to decide the robustness of the classifier.

Accordingly, it would be advantageous to develop systems and/or methods for classifying defects on a specimen with an adaptive automatic defect classifier that do not have one or more of the disadvantages described above.

SUMMARY OF THE INVENTION

The following description of various embodiments is not to be construed in any way as limiting the subject matter of the appended claims.

One embodiment relates to a system configured to classify defects on a specimen with an adaptive automatic defect classifier. The system includes an output acquisition subsystem that includes at least an energy source and a detector. The energy source is configured to generate energy that is directed to a specimen. The detector is configured to detect energy from the specimen and to generate output responsive to the detected energy. The system also includes one or more computer subsystems configured for detecting defects on the specimen based on the output generated by the detector to thereby generate first lot results. The one or more computer subsystems are also configured for separating the defects into different groups using a clustering method and receiving a classification for each of the different groups from a user. In addition, the computer subsystem(s) are configured for creating a defect classifier based on the received classifications and a training set of defects that includes all the defects in the first lot results. The computer subsystem(s) are further configured for detecting additional defects on another specimen of the same type as the specimen based on additional output generated by the detector for the other specimen to thereby generate additional lot results. The computer subsystem(s) are also configured for combining the first and additional lot results to create cumulative lot results and classifying the defects in the cumulative lot results by applying the created defect classifier to the defects in the cumulative lot results. In addition, the computer subsystem(s) are configured for determining if any of the defects in the additional lot results have a confidence value that is below a confidence threshold. The computer subsystem(s) are also configured for, when one or more of the defects in the additional lot results have a confidence value that is below the confidence threshold, receiving one or more classifications for the one or more defects from a user and modifying the training set to include the one or more defects and the one or more classifications. In addition, the computer subsystem(s) are configured for modifying the defect classifier based on the modified training set and classifying defects in the cumulative lot results with the modified defect classifier. The computer subsystem(s) are further configured for, when all of the defects in the cumulative lot results are classified by the user or none of the defects in the additional lot results have a confidence value that is below the confidence threshold, finishing adaptive classifier creation. The system may be further configured as described herein.

Another embodiment relates to a computer-implemented method for classifying defects on a specimen with an adaptive automatic defect classifier. The method includes steps for each of the functions of the one or more computer subsystems described above. The steps of the method are performed by one or more computer systems. The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executable on a computer system for performing a computer-implemented method for classifying defects on a specimen with an adaptive automatic defect classifier. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

Figure 1:
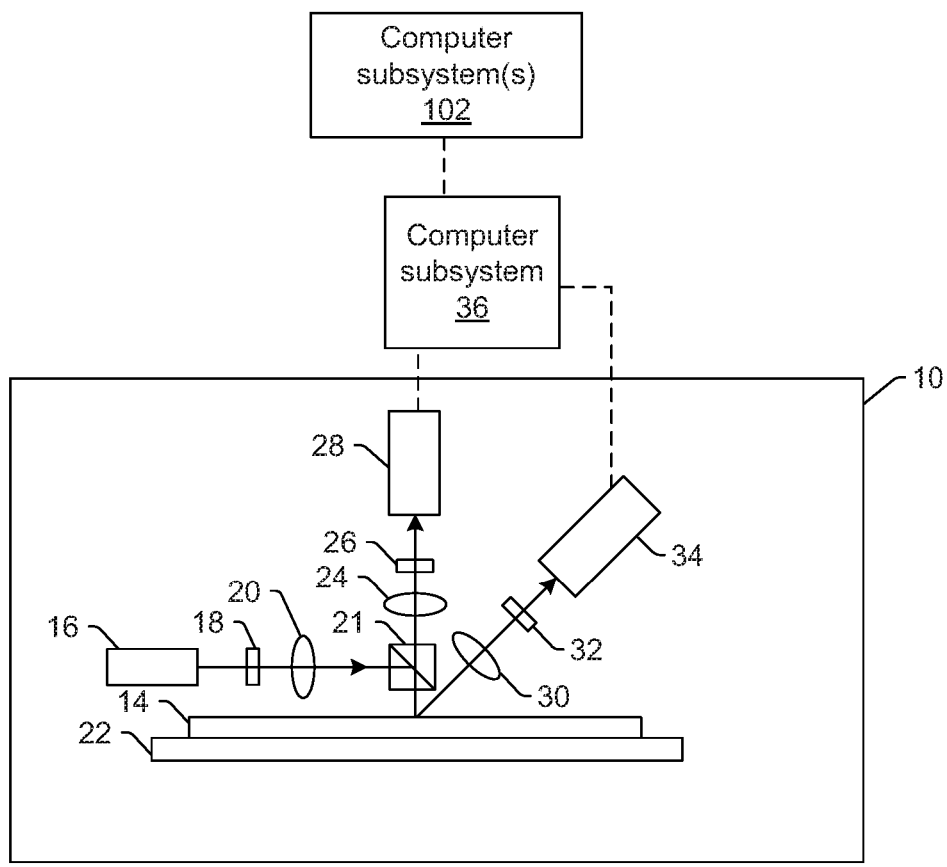
FIGS. 1 and 2 are schematic diagrams illustrating side views of embodiments of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to classify defects on a specimen with an adaptive automatic defect classifier. The embodiments provide an adaptive strategy to dynamically update and monitor a defect classifier for automatic defect classification (ADC) to adapt to the dynamic environment of a semiconductor fabrication process. The embodiments also provide a data redundancy score (DRS) generated using the adaptive strategy, where DRS can be used in conjunction with classifier training accuracy to determine the robustness of the classifier.

In one embodiment, the specimen includes a wafer. In another embodiment, the specimen includes a reticle. The wafer and the reticle may include any wafer and reticle known in the art.

One embodiment of such a system is shown in FIG. 1. The system includes an output acquisition subsystem that includes at least an energy source and a detector. The energy source is configured to generate energy that is directed to a specimen. The detector is configured to detect energy from the specimen and to generate output responsive to the detected energy.

In one embodiment, the energy directed to the specimen includes light, and the energy detected from the specimen includes light. For example, in the embodiment of the system shown in FIG. 1, output acquisition subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the output acquisition subsystem may be configured to alter one or more characteristics of one or more elements of the illumination subsystem such that the light can be directed to the specimen at an angle of incidence that is different than that shown in FIG. 1. In one such example, the output acquisition subsystem may be configured to move light source 16, optical element 18, and lens 20 such that the light is directed to the specimen at a different angle of incidence.

In some instances, the output acquisition subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for output acquisition.

The output acquisition subsystem may also include a scanning subsystem configured to cause the light to be scanned over the specimen. For example, the output acquisition subsystem may include stage 22 on which specimen 14 is disposed during output acquisition. The scanning subsystem may include any suitable mechanical and/or robotic assembly (that includes stage 22) that can be configured to move the specimen such that the light can be scanned over the specimen. In addition, or alternatively, the output acquisition subsystem may be configured such that one or more optical elements of the output acquisition subsystem perform some scanning of the light over the specimen. The light may be scanned over the specimen in any suitable fashion.

The output acquisition subsystem further includes one or more detection channels. At least one of the one or more detection channels includes a detector configured to detect light from the specimen due to illumination of the specimen by the output acquisition subsystem and to generate output responsive to the detected light. For example, the output acquisition subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect spectrally reflected light, and the other detection channel is configured to detect light that is not spectrally reflected (e.g., scattered, diffracted, etc.) from the specimen. However, two or more of the detection channels may be configured to detect the same type of light from the specimen (e.g., spectrally reflected light). Although FIG. 1 shows an embodiment of the output acquisition subsystem that includes two detection channels, the output acquisition subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the output acquisition system may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the output described herein in a number of ways.

It is noted that FIG. 1 is provided herein to generally illustrate a configuration of an output acquisition subsystem that may be included in the system embodiments described herein. Obviously, the output acquisition subsystem configuration described herein may be altered to optimize the performance of the system as is normally performed when designing a commercial inspection or defect review system. In addition, the systems described herein may be implemented using an existing output acquisition system (e.g., by adding functionality described herein to an existing output acquisition system) such as optical inspection and/or defect review tools such as the 28xx and 29xx series of tools that are commercially available from KLA-Tencor and other tools that are commercially available from other sources. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the output acquisition subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the output acquisition subsystem is described above as being an optical or light-based output acquisition subsystem, the output acquisition subsystem may be an electron beam-based output acquisition subsystem. For example, in one embodiment, the energy directed to the specimen includes electrons, and the energy detected from the specimen includes electrons. In this manner, the energy source may be an electron beam source. In one such embodiment shown in FIG. 2, the output acquisition subsystem includes electron column 122, which is coupled to computer subsystem 124.

Figure 2:
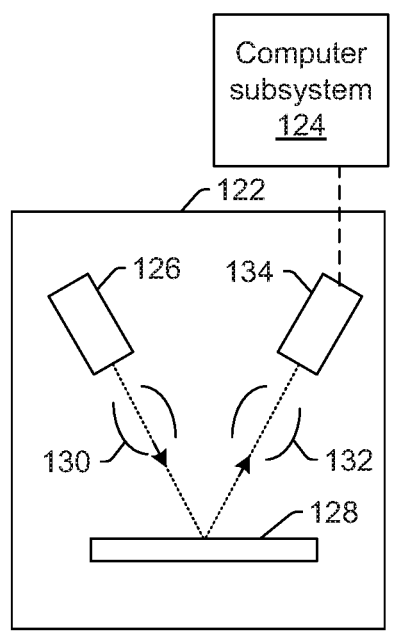

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based subsystem may be configured to use multiple modes to generate images of the specimen (e.g., with different illumination angles, collection angles, etc.). The multiple modes of the electron beam-based subsystem may be different in any image generation parameters of the subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the output acquisition subsystem shown in FIG. 2 may be further configured as described herein.

It is noted that FIG. 2 is provided herein to generally illustrate a configuration of an electron beam-based output acquisition subsystem that may be included in the embodiments described herein. As with the optical output acquisition subsystem described above, the electron beam-based output acquisition subsystem configuration described herein may be altered to optimize the performance of the output acquisition subsystem as is normally performed when designing a commercial inspection or defect review system. In addition, the systems described herein may be implemented using an existing defect review system (e.g., by adding functionality described herein to an existing inspection or defect review system) such as the eDR-xxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the output acquisition subsystem is described above as being a light-based or electron beam-based output acquisition subsystem, the output acquisition subsystem may be an ion beam-based output acquisition subsystem. Such an output acquisition subsystem may be configured as shown in FIG. 2 except that the electron beam source may be replaced with any suitable ion beam source known in the art. In addition, the output acquisition subsystem may be any other suitable ion beam-based subsystem such as those included in commercially available focused ion beam (FIB) systems, helium ion microscopy (HIM) systems, and secondary ion mass spectroscopy (SIMS) systems.

The one or more computer subsystems described above are configured for detecting defects on the specimen based on the output generated by the detector to thereby generate first lot results. The computer subsystem(s) described herein may be configured to detect the defects on the specimen in any suitable manner (e.g., by applying a threshold to the output and identifying output having one or more values above the threshold as a defect or potential defect and not identifying output having one or more values below the threshold as a defect or potential defect). The defects detected on the specimen may include any defects known in the art. The first lot results may include any information for the detected defects such as defect ID, defect location, attributes, output corresponding to the defects, and the like. In this manner, the computer subsystem(s) described herein may generate the lot results.

In some instances, however, the computer subsystem(s) do not necessarily generate the lot results. For example, the computer subsystem(s) may be configured to acquire lot results for the specimen. A user may select the lot results file to be used by the computer subsystem(s). The lot results include information for defects detected on the wafer by an inspection process and/or possibly a defect review process. The information may include information for one or more attributes of the defects. The one or more defect attributes may include any defect attributes that can be determined by an inspection or defect review system or from results generated by an inspection or defect review system. Examples of suitable defect attributes that can be used as described further herein include, but are not limited to, energy, magnitude, die coordinates, and design attributes. The lot results may include any other suitable information about the defects detected on the wafer such as the locations of the defects detected on the wafer and image data or images generated for the defects.

Figure 3:
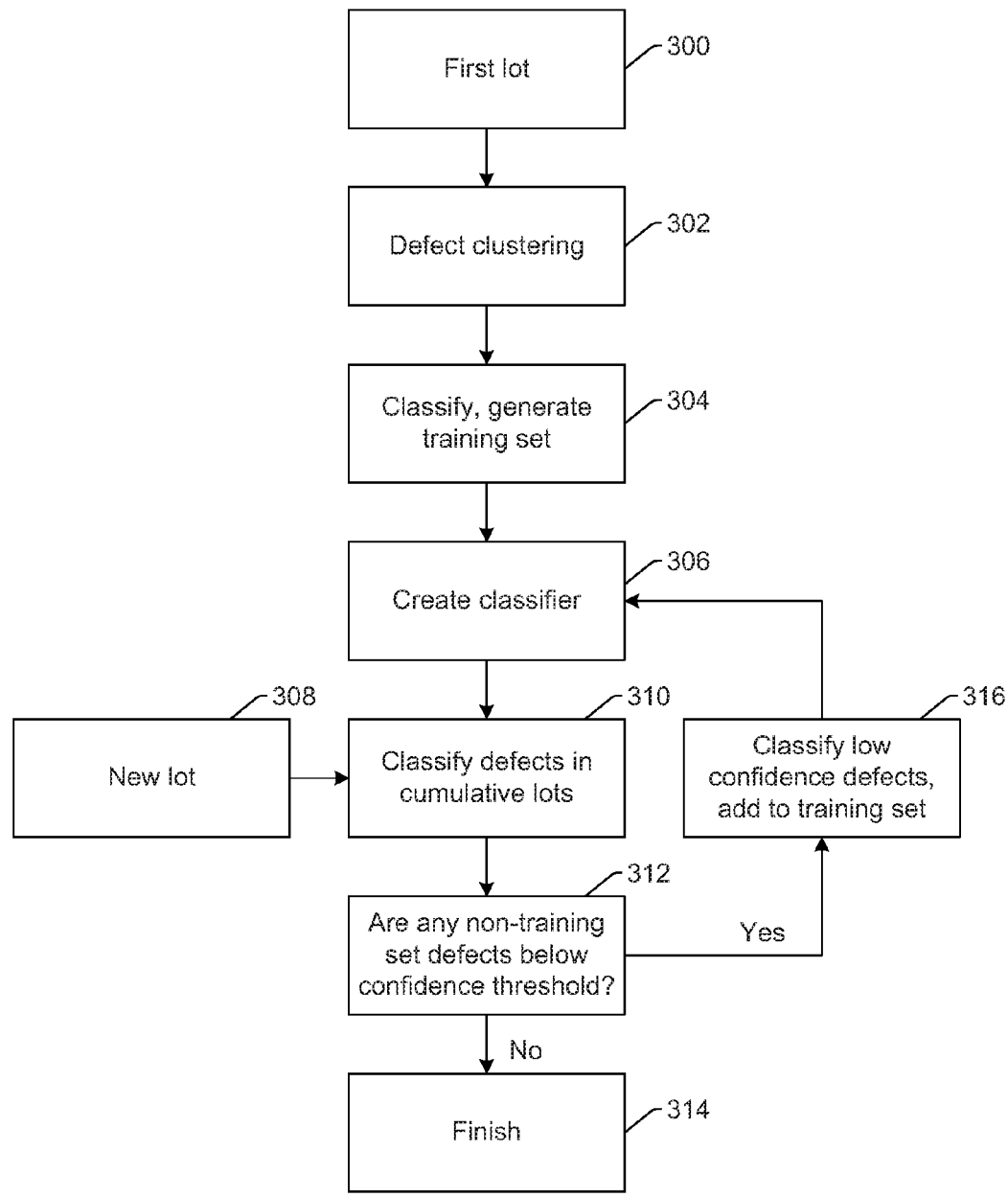
FIG. 3 is a flow diagram illustrating one embodiment of steps that may be performed by one or more computer subsystem embodiments described herein for classifying defects with an adaptive automatic defect classifier.

The computer subsystem(s) are also configured for separating the defects into different groups using a clustering method. For example, FIG. 3 shows steps that may be performed by one or more computer subsystems for adaptive automatic defect classification. As shown in this figure, the steps include defect clustering 302 performed based on first lot 300. The defect clustering method used to group the defects may be natural grouping or any other suitable defect clustering method (e.g., K-means, mean-shift, expectation-maximization (EM), etc.), which may be performed in any suitable manner known in the art.

The computer subsystem(s) are further configured for receiving a classification for each of the different groups from a user. For example, as shown in FIG. 3, the steps may include classifying the defects in step 304. In this manner, with the first lot results, all the defects may be classified by a user with guidance from natural grouping or another clustering method. For example, the computer subsystem(s) may display results of defect clustering 302 to a user with a suggestion as to the possible classifications for each of the different groups. The user may then accept one or more of the suggestions and/or enter a different classification from that suggested. As such, with the first lot, unlabeled defects may be classified by a user guided by a clustering method. The defects in the different groups may therefore be manually classified. Receiving the classification for each of the different groups from the user may be performed in any suitable manner.

The computer subsystem(s) are also configured for creating a defect classifier based on the received classifications and a training set of defects that includes all the defects in the first lot results. For example, as shown in step 304 of FIG. 3, this step may also include generating a training set. The training set may be created using all the defects in the first lot. The training set may be created in any suitable manner. As further shown in step 306 of FIG. 3, the steps may include creating a classifier. In this manner, a classifier may be created using defect data and classifications of a first lot, and as described further herein the defect classifier can be used for subsequent lots (i.e., second, third, etc. lot results).

In one embodiment, creating the defect classifier is performed with automatic confidence threshold. For example, the automated classifier may be created with auto confidence threshold, which can be used for assisted manual classification for the next lot results. In particular, creating a classifier with auto confidence threshold, using a random forest type classifier as an example, each defect may be assigned an out-of-bag class code and confidence (out-of-bag is similar to cross-validation). For each defect type, the confidence threshold may be increased from a minimum value (e.g., 0.7) until it reaches a purity target (such as 90%). The confidence threshold for each type is then recorded. Creating the defect classifier may, however, also be performed in any other suitable manner known in the art.

In one embodiment, the created defect classifier is a random forest type defect classifier. A random forest type defect classifier is a type of defect classifier that is generally known in the art. In general, a random forest type defect classifier includes multiple decision trees that operate in parallel. In this manner, any one defect may be input to each of the multiple decision trees. Then, the class that is assigned to any one defect may be determined based on the class or classes assigned to the defect by the multiple decision trees (e.g., via arbitration or some other technique).

In an additional embodiment, the created defect classifier is a supported vector machine (SVM) type defect classifier. An SVM type classifier is also a type of defect classifier that is generally known in the art. In general, an SVM type defect classifier analyzes data and recognizes patterns used for classification. For example, given a training set of data for different classes of defects, a model may be built that assigns new defects into one of the different classes. An SVM model is a representation of the training set as points in space that are mapped so that different categories are divided by as much space as possible. The SVM defect classifier may then map new defects into that same space and determine the classification of the new defects based on which of the different categories corresponds to the space in which the new defects are located. In this manner, the created defect classifier can be a random forest type defect classifier, an SVM type defect classifier, or any other suitable type of defect classifier known in the art.

The computer subsystem(s) are further configured for detecting additional defects on another specimen of the same type as the specimen based on additional output generated by the detector for the other specimen to thereby generate additional lot results. For example, as shown in FIG. 3, the computer subsystem(s) may generate new lot 308. The additional defects may be detected by the computer subsystem(s) as described further herein. The additional defects may include any of the defects described herein.

In addition, the computer subsystem(s) are configured for combining the first and additional lot results to create cumulative lot results. The first and additional lot results may be combined in any suitable manner.

The computer subsystem(s) are also configured for classifying the defects in the cumulative lot results by applying the created defect classifier to the defects in the cumulative lot results. For example, as shown in step 310 of FIG. 3, the steps performed by the computer subsystem(s) may include classifying defects in cumulative lots. In this manner, for any new lot, the defects in the new lot combined with all previous defects are classified using the created defect classifier. The created defect classifier may be applied to the cumulative lot results in any suitable manner.

The computer subsystem(s) are further configured for determining if any of the defects in the additional lot results have a confidence value that is below a confidence threshold. In other words, the computer subsystem(s) may be configured for determining if any of the additional lot results defects (or non-training set defects) are classified by the created defect classifier with a confidence that is below a confidence threshold and therefore assigned a confidence value by the created defect classifier that is below the confidence threshold. For example, as shown in step 312 of FIG. 3, the steps performed by the computer subsystem(s) may include determining if any non-training set defects are below a confidence threshold. The confidence threshold may be a predetermined threshold that is determined automatically or manually (by a user) and may vary depending on the defect classifier. In this manner, a confidence value assigned to each of the defects by the defect classifier may be compared to the threshold to determine if any of the defects have been assigned a confidence value that is below the threshold.

In addition, the computer subsystem(s) are configured for, when all of the defects in the cumulative lot results are classified by the user or none of the defects in the additional lot results (or the non-training set defects) has a confidence value that is below the confidence threshold, the steps performed by the computer subsystem(s) may include finishing the adaptive automatic defect classification (e.g., until another new lot is generated), as shown in step 314 of FIG. 3.

The computer subsystem(s) are also configured for, when one or more of the defects in the additional lot results have a confidence value that is below the confidence threshold, receiving one or more classifications for the one or more defects from a user and modifying the training set to include the one or more defects and the one or more classifications. For example, as shown in step 316 of FIG. 3, the steps performed by the computer subsystem(s) include classifying low confidence defects and adding the low confidence defects to the training set. In particular, if there are defects below the confidence threshold, a user may classify these defects using assisted manual classification and these defects are added to the training set. In one example of assisted manual classification, when a defect is an unknown type of defect, a user may be provided with a defect type suggestion from the embodiments described herein and then asked to input the defect type (e.g., by selecting or confirming the defect type suggestion and/or by inputting a new, different defect type).

The computer subsystem(s) are further configured for modifying the defect classifier based on the modified training set. For example, the automated classifier may be recreated using the new training set. In one such example, the modified training set may be input to step 306 shown in FIG. 3 and step 306 may be repeated with the modified training set to create a modified version of the defect classifier. These steps may be repeated until all the defects below a confidence threshold are manually classified by the operator. In addition, these steps may be performed as described further herein.

In addition, the computer subsystem(s) are configured for classifying defects in the cumulative lot results with the modified defect classifier. Classifying the defects with the modified defect classifier may be performed as described further herein. In addition, the computer subsystem(s) may be configured for classifying defects in additional cumulative lot results with the modified defect classifier. Classifying the defects in the additional cumulative lot results with the modified defect classifier may be performed as described further herein (e.g., by applying the modified defect classifier to the additional cumulative lot results). The additional cumulative lot results may include the first lot results, the additional lot results, and any other further lot results, which may be generated as described herein. In this manner, the modified defect classifier may be used to classify other new cumulative lot results that include all lot results generated up to that point.

Figure 4:
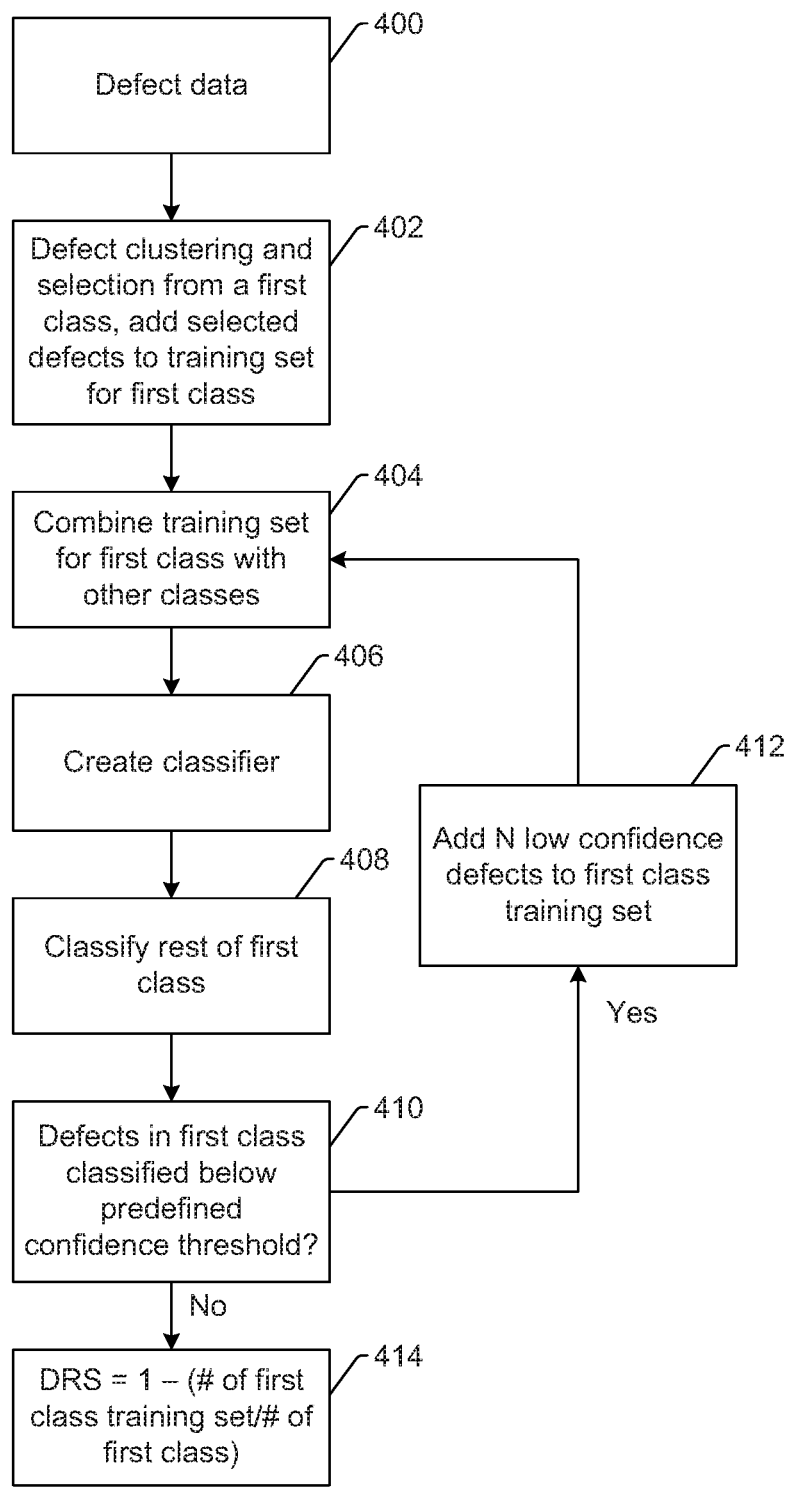
FIG. 4 is a flow diagram illustrating one embodiment of steps that may be performed by one or more computer subsystem embodiments described herein for determining a data redundancy score.

In one embodiment, the computer subsystem(s) are configured for determining a data redundancy score (DRS) by: a) for a first class of multiple classes of defects, selecting a portion of the defects in the first class using a clustering method and adding the selected portion of the defects to a training set for the first class. FIG. 4 shows one embodiment of steps that may be performed for DRS for the first class. As shown in step 402 of FIG. 4, the computer subsystem(s) may perform defect clustering based on defect data 400, selection of defects from the first class, and adding the selected defects to the training set for the first class. In this step, for all the defect data for the first class, natural grouping or another clustering method may be used to pick N defects from the first class and add them to the training set for the first class.

Determining the DRS also includes: b) creating an automated classifier with the training set for the first class and training sets of other classes of the multiple classes. For example, as shown in step 404 in FIG. 4, the computer subsystem(s) may be configured to combine the training set for the first class with other classes. In addition, as shown in step 406 of FIG. 4, the computer subsystem(s) may be configured to create a classifier. In this manner, an automated classifier may be created with the training set for the first class and all other classes. The classifier may be created as described further herein, and the created classifier may have any classifier type described herein.

In addition, determining the DRS includes: c) classifying a portion of the defects in the first class that were not selected in step a) with the automated classifier. For example, as shown in step 408 of FIG. 4, the computer subsystem(s) may be configured to classify the rest of the first class. In particular, the rest of the first class may be classified using the classifier created in step 406.

Determining the DRS further includes: d) if any defects in the first class are classified below a predefined confidence threshold by the automated classifier, adding a predetermined number of the defects in the first class to the training set for the first class and repeating steps a) to c). For example, as shown in step 410 of FIG. 4, the computer subsystem(s) may be configured for determining if defects in the first class are classified below a predefined confidence threshold, which may be performed as described further herein. In addition, as shown in step 412 of FIG. 4, the computer subsystem(s) may be configured for adding N low confidence defects to the training set for the first class, which may be performed as described further herein. In this manner, if there are any defects in the first class below a predefined threshold C, N defects may be added to the training set for the first class, and the computer subsystem may repeat steps 404, 406, 408, and 410 shown in FIG. 4. The value of N in this step may include any suitable value.

Determining the DRS also includes: e) if none of the defects in the first class are classified below the predefined confidence threshold by the automated classifier, calculating the data redundancy score as equal to 1–(size of the training set for the first class) divided by (size of the first class). For example, as shown in step 414 of FIG. 4, if there are no defects in the first class below a predefined threshold C, the computer subsystem(s) may calculate the DRS according to DRS=1–(size of training set for the first class)/(size of the first class). The DRS may therefore be used to evaluate the robustness of a defect classifier (i.e., if the classifier is created with sufficient data). For example, if the DRS score meets some predefined criteria (such as greater than 0.4 in one example), it may be determined that the classifier has been created with sufficient data and is robust. The classifier can then be released to production.

The embodiments described above have a number of advantages over previously used methods and systems for ADC. For example, the embodiments provide a created defect classifier with the first available lot results. The created defect classifier can be used for assisted manual classification. In this manner, the classifier can be in production much earlier, and the customer can see the contribution of the classifier sooner. Contribution can be defined as (# of defects of a defect type that have a purity greater than 90%)/(Total defects). In this manner, the contribution is essentially the ratio of defects that do not need human review.

In addition, the embodiments described herein provide adaptation to dynamic changes in the defect characteristics and classifications (e.g., a defect pareto) and tool drift. In particular, since the classifier is re-trained for every new lot, it can adapt to any changes of tool, imaging, or process in situ. The created classifier also adapts to the dynamic changes of defect data much faster thereby increasing the value of the classification. In this manner, the embodiments described herein provide adaptive ADC that adapts to the defect environment of semiconductor fabrication. Furthermore, the embodiments described herein eliminate the need for training, validation, and production phases since the classifier is always and continuously retrained.

Moreover, the embodiments described herein improve cost of ownership since less time is spent on performing manual review. For example, since after the first lot results, the user only needs to classify defects below the confidence threshold, over time the user will only need to classify, for example, 20% of the defects (if the contribution is 80%). In this manner, the embodiments described herein can update the classifier dynamically by manually reviewing a relatively small portion of the defects. Therefore, the embodiments described herein help a user to reduce cost of tool ownership since the user only has to manually review a relatively small portion of the defects. In addition, the assisted manual classification provided by the embodiments described herein shortens the manual classification time. In other words, the embodiments described herein help users with manual classification because the initial classifier can be used for assisted manual classification.

The embodiments described herein also provide a balanced training set that can be used to create a robust and better classifier. A balanced training set may be one that includes the same number (or nearly the same number) of examples of all defect types (e.g., 10 particles, 10 residues, 10 scratches as opposed to 1 particle, 1 residue, and 28 scratches). For example, in many cases, defect data contains more than 90% nuisance and these nuisance defects are classified with substantially high confidence. Since only those defects falling below the confidence threshold are manually classified and added to the training set in the embodiments described herein, there will be more DOIs in the training set and the defects in the training set are better balanced. The classifier created using the balanced training set is more robust and has higher accuracy compared to the previous method since the training set is more balanced and includes more DOIs.

The embodiments described herein can also be used to calculate and provide a DRS that can be used to determine the robustness of the classifier for each class. If the DRS is larger than zero, it indicates that there is already enough defect data to create the classifier for the class.

Some additional embodiments described herein use results of a defect classifier as a diagnostic for classifier degradation in production due to tool drift. Some currently used ADC methods, for review, use a classifier such as a random forest type defect classifier as a classifier engine to provide ADC to a user of a defect review tool. However, over time, the imaging conditions of defect review tools can vary significantly on the tools, a process known as tool drift, due to variation in one or more parameters of the output acquisition subsystem such as, in the case of an electron beam based tool, the beam current and iRaw (total current obtained from the electron beam source of the electron beam tool), or in the case of a light based tool, the light directed to the specimen by the tool and the light generated by a light source of the tool. This variation in tool conditions over time can cause the attributes used by the classifier to drift leading to classifier performance degradation over time. For example, iRaw current is directly correlated to the intensity/brightness levels of image pixels and therefore possibly any attributes determined from such image pixels. Therefore, it is desirable to control the iRaw current to ensure the images have similar brightness levels.

However, the direct relationship between tool drift and attribute drift can be unknown and depend on a variety of factors such as defect types, layer background, imaging conditions, etc. Further, some classifiers may be more robust to attribute drift as compared to other classifiers. For example, a classifier in which the defects types are well separated may be more robust to attribute drift than a classifier with defect types that are harder to separate in the attribute space. Furthermore, a classifier based on topographical defects alone has been found to be more stable to tool drift as compared to a classifier based on contrast-based defects since intensity-based attributes tend to drift more with tool drift as compared to topographical attributes.

Some current solutions in development aim at directly monitoring beam current and iRaw as a measure to ensure tool conditions remain within specification. For example, to guard a classifier against tool drift, some current techniques performed on electron beam based defect review tools monitor the beam current and iRaw of the tool. Data collected when the tool is out of specification range on either of the two is not used for classifier training, and calibration is triggered on the tool to bring the tool back into specification.

Since the relationship between tool drift and attribute drift can be unknown, in another possible technique being tested, a manual decision tree is created on a standard wafer used for calibration. The decision tree makes a check on the range of the most susceptible intensity attributes and ensures that the attributes are within range for the standard wafer. Thus, if the attributes on the standard wafer are within specification, the tool may be released to production.

There are, however, a number of disadvantages to the approaches described above. For example, in the beam current and iRaw monitoring methods, the tool drift is directly measured but does not take into account the effect of the tool drift on the classifier. In other words, monitoring tool parameters such as iRaw, beam current, and mean gray level may give an idea of tool drift, but it may not be possible to know whether this tool drift affects the classifier or not. In this manner, if the classifiers in production are relatively stable to tool drift, unnecessary calibrations may be performed if the beam current and iRaw are out of specification. The specification is predefined globally. In addition, if the classifiers used in production are relatively unstable to tool drift, the classifier performance may have degraded but iRaw and beam current may still be within specification. Therefore, coming up with global bounds on iRaw and beam current is unrealistic since appropriate bounds vary by classifier and defect type on the layer. If the specifications are too tight, they would result in a large number of false alarms. In contrast, if the specifications are too loose, they would result in many classifiers being used in production with degraded performance.

In the defect classification performed with a standard wafer, though this technique is an improvement over the previous technique in that it aims to estimate the effect on attributes due to tool drift, it only measures attribute and classifier performance on a standard wafer. Such measurements cannot be generalized across classifiers since the effect of tool drift is unique to each classifier depending on defect types and separation in attribute space of the defect types. Thus, even this method cannot estimate the effect of tool drift on the classifier performance per classifier and suffers the same drawbacks as the previous approach.

The relationship between the tool drift and classifier performance degradation varies, therefore, from classifier to classifier and defect type to defect type. In production, where the user does not verify the ADC suggested bin codes, there is no ground truth data and thus no way of directly estimating classifier performance degradation. However, as described further herein, the embodiments described herein may be configured to directly monitor results of a defect classifier such as rejected bin size and/or confidence histogram to directly diagnose any drop in classifier performance for the defect type due to attribute shift caused by tool drift over time. Every defect bin can be analyzed individually for drop in performance due to tool drift.

In one embodiment, the computer subsystem(s) are configured for monitoring a size of a bin of unclassified defects in results produced by the created defect classifier and the modified defect classifier and generating an alarm when the size of the bin is greater than a predetermined size, and the alarm indicates that calibration of one or more parameters of the output acquisition subsystem is necessary. For example, the embodiments may use an increase in rejected bin size to detect increasing attributes drift. In particular, some defect classifiers classify defects with only high confidence to defect bins. A confidence threshold on each defect bin may be applied, and defects below the threshold may be sent to a rejected bin, to be manually classified by a user. In this manner, the embodiments may monitor the rejected bin size of the classifier and raise an alarm that performance of a defect bin is being affected by tool drift. As such, the embodiments may be configured for triggering of beam recalibrations using rejected bin size as an indicator of classifier performance degradation.

In a further embodiment, the one or more computer subsystems are configured for monitoring a confidence histogram of each defect bin in results produced by the created defect classifier and the modified defect classifier and generating an alarm when the confidence histogram has one or more predetermined characteristics, and the alarm indicates that calibration of one or more parameters of the output acquisition subsystem is necessary. For example, the embodiments may use a drop in average confidence for the defect bins as attributes drift. In this manner, the embodiments may monitor the confidence histogram of each defect bin and raise an alarm that performance of a defect bin is being affected by tool drift. As such, the embodiments may be configured for triggering of beam recalibrations using confidence histograms as an indicator of classifier performance degradation.

In particular, a confidence may be assigned by a classifier to each defect. This confidence is the confidence the classifier has that the defect type of this defect is actually the type that the classifier has assigned to it. The confidence per defect bin can be visualized by assigning a confidence level to every region in the attribute space. Regions with substantially high density of the defect type are given a relatively high confidence while regions where the density is lower are assigned lower confidence.

As the tool drifts over time, the attributes cloud of each defect type starts to shift. Thus, the defects of a particular defect type start moving out of regions that they previously populated in attribute space, i.e., regions where confidence was high. Thus, we would expect that as the tool drifts, the confidence histogram would move from relatively high confidence to medium confidence and gradually to low confidence. In addition, as the histogram moves towards lower confidence, more and more defects would end up under the confidence threshold of each defect type by the classifier and thus the rejected bin size would increase over time. Thus, the embodiments described herein can monitor the rejected bin size and/or confidence histogram of each defect type to measure the effect of tool drift directly on classifier performance. As such, the embodiments described herein can be used for monitoring classifiers against tool drift using a confidence measure output by a classifier. In addition, the embodiments described herein can be used for classifier monitoring against tool drift in production in situations in which no ground truth data is available.

In some embodiments, the one or more computer subsystems are configured for determining a robustness score for the created defect classifier by perturbing the training set in one or more attributes of the defects used by the created defect classifier for classifying the defects and determining an amount of perturbation the created defect classifier can withstand before performance of the created defect classifier drops below a predetermined level. In this manner, the embodiments described herein may assign a robustness score to each classifier, which estimates how much attribute drift a classifier can tolerate. The training set may be perturbed in the attribute space, and the amount of perturbation that it can withstand before classifier performance starts to drop (e.g., by a certain, predetermined percentage) is defined as the robustness score of the classifier. Therefore, one advantage of the embodiments described herein is that they can define a robustness score per classifier, a measure of immunity of the classifier to tool drift.

In one such embodiment, the computer subsystem(s) are configured for determining one or more control settings for one or more parameters of the output acquisition subsystem based on the robustness score. For example, if, in a fab, a relatively large number of classifiers have a relatively low robustness score, tighter specifications on beam current and iRaw for example in the case of an electron beam based tool would be desirable, while if all the classifiers have a relatively high robustness score, the specifications can be looser. Thus, the embodiments described herein can be used as a standalone method or using robustness score can be used with the tool drift monitoring approach to define the bounds on the specifications.

In contrast to the embodiments described herein, therefore, currently used methods aim at estimating tool drift in terms of tool parameters or performance degradation in terms of classification performed on a standard wafer. Unlike those methods, the embodiments described herein directly estimate the performance degradation per defect bin per classifier. Therefore, one advantage of the embodiments described herein is that they can directly estimate classifier degradation per classifier due to tool/attributes drift. Previous approaches do not have estimations per classifier, just at tool level or standard wafer-specific measurement. In addition, an advantage of the embodiments described herein is that they can directly estimate classifier degradation per defect type per classifier due to tool/attributes drift. Previous approaches do not have estimations per defect type per classifier, just at the tool level or standard wafer specific measurements. The rejection bin percentage and the shift in confidence histogram can be thresholded to raise an alarm for performance degradation. This alarm for degradation can be used to recalibrate the tool. Previous methods suffered from the drawback that they can trigger recalibration either when none of the classifiers has degraded, i.e., in the case of false positives, or they can fail to trigger recalibration when a classifier has actually degraded, i.e., the failure cases. In this manner, previous approaches could have a classifier running in a degraded mode if the tool was still within specification, e.g., with respect to beam current and iRaw. The embodiments described herein do not suffer from either of these drawbacks and they directly monitor classifier degradation due to tool drift. For example, one advantage of the embodiments described herein is that they greatly minimize the number of false alarms for beam calibrations or other image-related calibrations of the tool as compared to the previous approaches. In addition, another advantage of the embodiments described herein is that they ensure that no classifier is running with degraded performance in production. The embodiments described herein can also be used to determine if a classifier ported from one tool to another tool is working on the other tool, i.e., the tool states match, without requiring the user to classify data to validate the classifier.

In this manner, the embodiments described herein may play a critical role in monitoring classifiers in production for performance degradation due to tool drift. The embodiments provide a set of direct measures for estimating classifier performance degradation due to tool drift and triggering recalibration of the tool rather than relying on defining hard bounds of measurements of tool performance. Additionally, such bounds are hard to estimate. In addition, as noted above, current solutions might trigger recalibration even when no classifier performance has degraded, which has a lot of time cost involved, requiring the tool to be pulled out of production. Similarly, a classifier might degrade even though the tool is within specification of the bounds defined, and a user could lose trust in the classifier. The embodiments described herein provide a direct solution to both of these issues.

Some additional embodiments described herein are configured for novelty detection in production for ADC. Current ADC methods for defect review provide users with a classifier for each layer, and each classifier differentiates and labels all the different defect types occurring on the layer. These classification results help the user to track defect classification results (e.g., a defect pareto) on the layer and monitor excursions and process changes. However, since the classifiers are trained on a particular set of defects, which are present in the training set, they are unable to catch and differentiate any new type of defect that occurs on the layer during production.

The ability to catch novel defects is of high importance to the user since novel defects signal a variation in the process performed on the layer, and if the novel defect is critical, it may render the wafers unusable. Therefore, the user wants to catch these novel defects as quickly as possible.

The occurrence of novel defects is also important for ADC, as ADC preferably is configured for stable classifier performance over time. Due to process change on the layer, novel defects can occur on the layer, which can cause the classifier performance to degrade as the novel defects start getting classified into other defect classes. Thus, currently used ADC is susceptible to performance degradation due to process change. Hence, it is important to have novel defect detection for production use cases in order to detect new defects on the layer as well as to trigger re-training of the classifier with the new defect class.

Since there can be significant variation in the defects of existing defect classes as well, defects having significant variation can act as novel defects with respect to the classifier, but these are not defects that are interesting to catch. To ensure pure novel defect detection, the embodiments described herein detect clusters of novel defects, i.e., the novel defects that are sufficient in number to form cluster(s), and at the same time are most different from existing defect classes.

The embodiments described herein can be used for detecting novel defects occurring on wafers running in production. The results produced by the embodiments described herein can be used to inform the user of any process drift on the layer in addition to guarding the classifier against performance degradation due to process drift. Additionally, once the size of the novel defect bin exceeds a threshold, the novel defect bins can be classified by the user and trigger re-training of the classifier.

Studies done in developing ADC for electron beam based defect review have previously compared use of random forest confidence and proximity based outlier measures to detect novel classes, and random forest confidence based outlier measure was proven more effective for novel detection. In random forest confidence based novel detection, random forest classification assigns a class code and a confidence level to each defect. Novel detection is done by pruning out the defects with the lowest random forest confidence, i.e., defects that the classifier is unable to classify.

In addition to the machine learning domain, 1-class classifiers are the state of the art to differentiate between seen and unseen data (where seen data is the data available in the training phase of the classifier and unseen data is the data that will come in the future on which a classifier can be tested). These classifiers build models based on the training data and assign the production data with a confidence that it is similar to seen data. This can be thresholded to obtain novel defects.

There are, however, a number of disadvantages to the currently used methods and systems. For example, in the random forest confidence based novel detection, significant variation in the defects of existing classes causes them to be classified with low random forest confidence, and these get classified as novel defects. That is, even though these defects may be novel with respect to the classifier, intra-class variations are not of interest. In addition, if there are two similar classes on a given layer, for example, particles and residues, random forest would be able to classify them only with low confidence as it is unable to differentiate between the two classes. Thus, these classes of defects may end up in the novel bin as well. Furthermore, to guard against classifier performance degradation and trigger re-training of classifiers, catching clusters of novel defects with significant numbers is more interesting that a class of novel defects with one or two defects each, in production. Even if it is possible to catch a set of novel defects with one or two examples in production, random forest classifiers cannot be trained for that class due to lack of data. In this regard, random forest confidence based novel defect detection is unable to provide any clustering of the novel defects to thereby provide major bins and prune out novel defects with few examples. Moreover, novel classes can be erroneously assigned with high confidence to another class present in training. Due to the disadvantages described above, this approach has relatively low accuracy with a relatively large number of false positives.

In another example, in the one class classifiers, the choice of model is difficult. A number of models are known but selecting the number of clusters etc. is hard and affects performance of novel defect detection. In addition, such classifiers are unable to differentiate between clusters of novel defects and variations in defects of existing classes, which it ends up classifying as novel defects. Furthermore, such classifiers threshold 5% of the training data defects as outliers and model the problem as a 2 class problem using 5% and 95% of the training data (threshold of 5% is manually modifiable) as the two classes. Thus, outlier detection is significantly dependent on the training data.

ADC classifiers used in production classify the defects into defect bins and a rejected bin. The rejected bin includes defects the classifier is unable to classify with high confidence. The rejected bin may include both novel classes as well as existing defect types on the layer. Additionally, some of the novel class defects may have been classified to the defect bins as well.

Some of the embodiments described herein use the fact that, for the defects in the rejected bin that belong to classes already in the original training data set, the classifier would be unable to classify them as novel defects with relatively high confidence while the defects that belong to a novel class and are different from the training set defects get classified as novel defects with relatively high confidence. For example, in one embodiment, the computer subsystem(s) are configured for appending defects in a bin of unclassified defects produced by the created defect classifier or the modified defect classifier to the training set or the modified training set, respectively, thereby creating an additional training set. For example, in the embodiments described herein, the rejected bin defects may be appended to the original training data set used for classifier setup and given a unique class code (e.g., 256) for training. In another example, for all x lots in the production lots, all the rejected bin (e.g., class 256) defects may be labeled to another class code "Rejected." These defects may then be appended to the original training data set or the most recent training data set. In this manner, the training data may then include the rejected bin.

Figure 5:
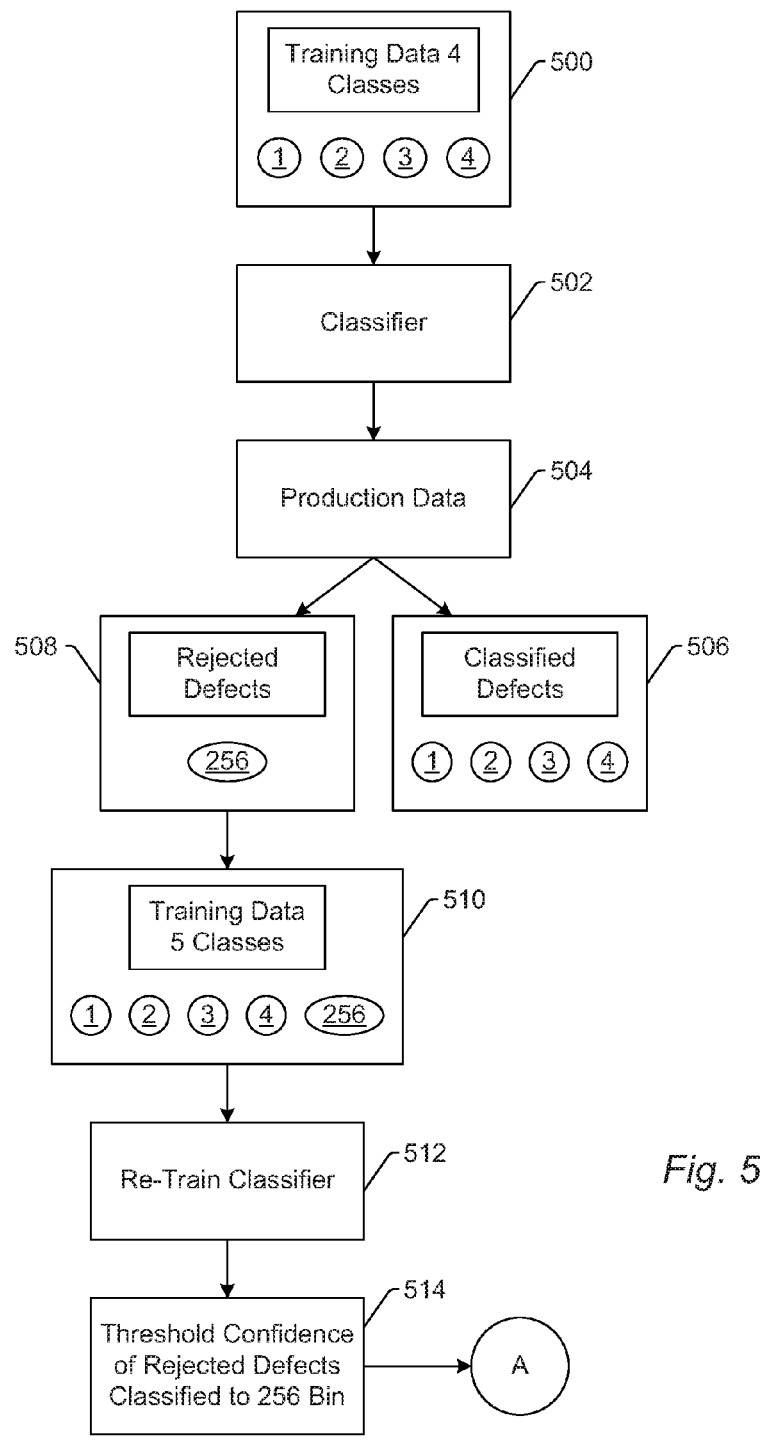
FIG. 5 is a flow diagram illustrating one embodiment of steps that may be performed by one or more computer subsystem embodiments described herein for novel defect detection.
Figure 5:
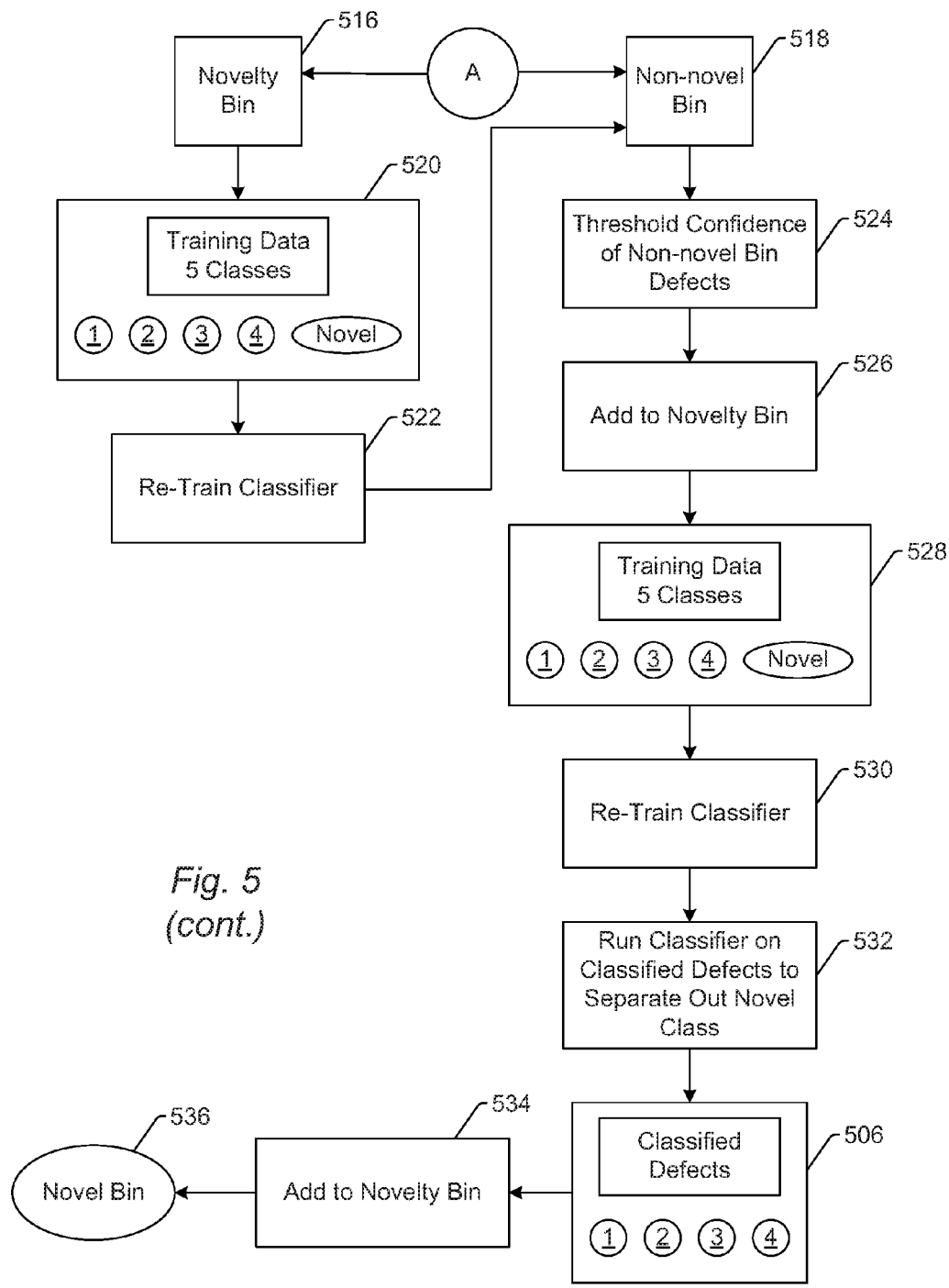

In one such example, as shown in FIG. 5, training data 500 for 4 classes, 1, 2, 3, and 4, may be input to classifier 502. The training data may be used to train classifier 502, which may then be used to classify defects in production data 504. Results of applying classifier 502 to production data 504 may include classified defects 506 and rejected defects 508. The classified defects may include any number of defects classified into the classes, 1, 2, 3, and 4, included in the training set, while the rejected defects may include any defects included in the production data that could not be classified into one of the classes included in the training set. In this manner, the rejected defects may be considered unclassified defects and may be assigned a different bin or class number, e.g., such as bin 256 as shown in FIG. 5. In particular, classifiers such as the random forest classifier may prune out defects that have been assigned to classified defect bins with relatively low confidence and send them to the rejected bin. In this manner, the random forest confidence value for defects in production data itself does not prove sufficient to filter out the novel class defect clusters from other low confidence defects of existing classes, i.e., a novel class does not necessarily have the lowest random forest confidence. The embodiments described herein can be used to filter out clusters of new defects and new sub-types of defects from other low confidence defects.

Rejected defects 508 may then be appended to the training data 500. In this manner, as shown in FIG. 5, additional training set 510 may be created by appending the rejected defects to training data 500. In addition, as shown in FIG. 5, the additional training set will include all of the classes included in the original training data as well as a class, e.g., 256, for the rejected defects.

In such an embodiment, the computer subsystem(s) are configured for training another classifier on the additional training set, and the other classifier classifies two or more of the defects in the additional training set to an additional bin of unclassified defects. For example, another classifier (of the same type) or the same classifier may be trained on the appended data set. In this manner, the classifier may be re-trained with the training class codes as well as the rejected class codes. In one such example, as shown in FIG. 5, additional training set 510 may be used to re-train classifier

512. As a result of this re-training, because additional training set 510 includes defect classes as well as a class for rejected defects, the re-trained classifier will classify defects into the defect and rejected classes, e.g., defect classes 1, 2, 3, and 4 and rejected class 256.

In addition, in such an embodiment, the computer subsystem(s) are configured for separating the defects in the additional bin of unclassified defects based on confidence of the other classifier assigned to each of the defects in the additional bin such that the defects having a confidence above another confidence threshold are assigned to a first bin and defects having a confidence below the other confidence threshold are assigned to a second bin, and the first bin is a preliminary novel bin. For example, the out-of-box (OOB) confidence (as in the case of random forest) or the k-folds cross-validation confidence (as in the case of SVM) of the defects classified as bin 256 may be used as a threshold by the classifier to obtain the preliminary novel bin. In one such example, as shown in step 514 of FIG. 5, the computer subsystem(s) may threshold the OOB confidence of the rejected defects classified to the rejected (or 256) bin thereby separating the rejected defects into novelty bin 516 and non-novel bin 518. In other words, clusters of novel classes that are well differentiated from training classes can be separated out and become the novel bin. The defects classified to the rejected bin 256, but with an OOB confidence below the threshold, may be saved to another non-novel bin. In this manner, defects in the rejected bin above a threshold may be sent to a novel class and the rest of the defects may be sent to another bin (e.g., non-novel bin). Therefore, the embodiments described herein may define a novelty defect confidence. Previously used random forest confidence based approaches assign (1—random forest confidence of the assigned random forest code) as the novel bin confidence per defect. In contrast, the confidence thresholds described herein provide a parameter tunable by a user to vary the accuracy versus purity of the novel bin, depending on their needs, catching all novel defects that are important or maintaining purity of the novel bin that is important with relatively few false positives. For cases in which a user is not available to mark the threshold, an automatic threshold may be used. An automatic threshold may be determined based on the number of novel defects having a confidence above x that is greater than a number of defects y. For example, a threshold of 0.9 may be used if the number of novel defects having a confidence above 0.9 is greater than 30. In this manner, the thresholds may be chosen in a way to ensure that sufficient novel defects are present in the novel bin to ensure that training can be performed as described further herein.

Furthermore, in such an embodiment, the computer subsystem(s) are configured for appending the preliminary novel bin to the training set or the modified training set, respectively, thereby creating a further training set, and the computer subsystem(s) are configured for training an additional classifier on the further training set. For example, the preliminary novel bin may be appended to the training data set to train another classifier or to re-train the classifier. In one such example, as shown in FIG. 5, the computer subsystem(s) may create further training set 520 that includes 5 classes, defect classes 1, 2, 3, and 4 and preliminary novel bin 516. As shown in step 522 of FIG. 5, the computer subsystem(s) may then re-train the classifier using further training set 520. After completion of re-training with the novel bin and the original training data, the OOB confidence of the novel class defects is defined as the novel defect confidence, i.e., the confidence with which the defect belongs to a novel class.

Moreover, in such an embodiment, the computer subsystem(s) are configured for classifying the defects assigned to the second bin with the additional classifier to thereby separate the defects assigned to the second bin into defects assigned to the second bin with a confidence above an additional confidence threshold and defects assigned to the second bin with a confidence below the additional confidence threshold. For example, this classifier may be re-run on the non-novel bin, and a confidence threshold may be used to prune out defects similar to the novel bin from the non-novel bin. In one such example, the classifier re-trained in step 522 may be applied to non-novel bin 518, and, as shown in step 524, the computer subsystem(s) may threshold the confidence of the non-novel bin defects as assigned by the classifier. In this manner, defects above a threshold for the novel class can be sent to the novel bin. In other words, after re-running the classifier trained as described above on defects in non-novel defect bin 518, some defects in non-novel defect bin 518 may be re-classified by the classifier as novel bin defects in this step with some confidence. These defects may be thresholded on the confidence, added to the novel class bin, and given the novel defect confidence as the confidence of this classifier. After this step, the novel defects will have been recovered from the rejected bin. In addition, this step may obtain the defects belonging to the novel bin as well as assigns a novel detection confidence to them.

In addition, in such an embodiment, the computer subsystem(s) are configured for adding the defects assigned to the second bin with the confidence above the additional confidence threshold to the preliminary novel bin to thereby create a final novel bin. For example, as shown in step 526 of FIG. 5, the computer subsystem(s) may be configured for adding results of step 524 to the novelty bin 516, which may be performed in any suitable manner.

In one such embodiment, the computer subsystem(s) are configured for appending the defects in the final novel bin to the training set or the modified training set, respectively, thereby creating another further training set, re-training the created defect classifier or the modified defect classifier, respectively, based on the other further training set such that the re-trained defect classifier produces an additional novel bin corresponding to the first novel bin, and classifying the defects in one or more bins other than the bin of unclassified defects produced by the created defect classifier or the modified defect classifier, respectively, with the re-trained defect classifier such that the defects in the one or more bins that are novel defects are moved from the one or more bins to the additional novel bin. For example, the final novel bin may be used to further re-train the classifier by appending the novel bin to the original training data set and re-running the further re-trained classifier on the defect bin(s). In one such example, as shown in FIG. 5, training set 528 may be created by adding the defects in the final novel bin created by step 526 to the training set. Therefore, the training set will include defect classes 1, 2, 3, and 4 and a novel defect class. As further shown in step 530 of FIG. 5, the computer subsystem(s) may be configured for re-training the classifier using training set 528. In addition, as shown in step 532 of FIG. 5, the computer subsystem(s) may be configured for running the classifier on the originally classified defects (e.g., classified defects 506) to separate out the novel class from the classified defects. As further shown in step 534 of FIG. 5, the defects in classified defects 506 that are separated out as being novel defects may be added to the novelty bin (e.g., novelty bin 516) to thereby create additional novel bin 536. These steps separate novel defects from the defects classified with relatively high confidence by the currently used ADC classifier. In other words, this classifier can be rerun on the defect bins, the defects classified by the original classifier, to obtain the overall novel class. As such, novel class defects that got sent to a classified bin by the original classifier can be pruned out.

The embodiments described herein have a number of advantages over other methods for detecting novel defects. For example, the embodiments described herein provide significantly higher accuracy and purity of the novel bin. In particular, the embodiments described herein provide a significant improvement by using a new approach compared to currently used methods and systems. The embodiments described herein obtain a much higher accuracy at the same level of purity as compared to a random forest based confidence approach, i.e., they are able to maximize the number of novel defects in the novel bin, which is the accuracy, while at the same time maintaining the purity of the novel bin, i.e., minimizing the number of false positives. To report the same number of defects as the novel bin, the random forest based approach reports a lot more false positives, which might lead to a relatively large number of false alarms during classifier monitoring and might trigger unnecessary re-training of classifiers.

The embodiments described herein may also be configured to use the novel bin as a threshold to trigger classifier re-training. In particular, the embodiments described herein may be configured for using novelty bin size to trigger classifier re-training with the novel class. In this manner, the computer subsystem(s) may be configured to monitor a layer for a process change and raise a flag if significant novel class defects are detected. For example, when a new class of defects appears on a layer, the classifier should be re-trained such that it can classify that new class. One of the challenges for the production use case is not only detecting a novel class but also determining when a sufficient number of novel defects have been collected to trigger classifier re-training with the novel bin. To train the classifier for a new class, the random forest classifier requires a minimum of 20-30 defects of the novel bin. In other words, the random forest technique requires at least 20-30 defects per class to re-train the classifier. Thus, it would be advantageous to trigger classifier re-training only when a novel class with greater than 20-30 defect examples is detected. In one such embodiment, the one or more computer subsystems are configured for comparing a size of the final novel bin to a threshold and triggering re-training of the created defect classifier or the modified defect classifier, respectively, when the size of the final novel bin is above the threshold. In this manner, the embodiments described herein may be able to detect relatively large clusters of novel defects and trigger re-training of classifiers with the novel bin when the novel bin exceeds a certain limit. Re-training a classifier is a costly process in which manual classification has to be performed for the new defects and re-training of the classifier has to be triggered on the tool. Thus, making an automated decision regarding when a sufficient number of a novel type of defects is available to trigger re-training of the classifier can have a high cost attached to it if the trigger is incorrect. The embodiments described herein can advantageously catch mostly defects in novel classes with greater than 20-30 defect examples with some of the defects that are incorrectly caught as novel defects.

Using novelty bin size to trigger classifier re-training for novel defects as described herein would have a higher re-train success rate as compared to other approaches. For example, in other approaches, classifier re-training may be triggered without having sufficient data available for the novel class that can be used for re-training. Compared to the embodiments described herein, in the random forest based approach, the novel bin includes both relatively large clusters of novel bin defects (i.e., novel classes with greater than 20-30 defect examples), a relatively large number of novel defect classes each having relatively few examples (i.e., novel classes with less than 20 defect examples), as well as a relatively large number of false positives (i.e., defects incorrectly caught as novel defects). In this case, even though a significant number of novel defects may be collected in the novel bin, the classifier may not be re-trainable if there are too many novel classes with few defect examples or there are relatively large numbers of false positives. Thus, the novel bin size cannot be used as a threshold for re-training in the random forest confidence threshold method. In other words, thresholding the number of defects in a novel bin to trigger automatic re-training will be effective in the embodiments described herein but ineffective in random forest confidence based approaches as many of the defects in a novel bin with greater than 20-30 defects can be defects that belong to novel defect classes with less than 20 defect examples in the novel bin as well as defects incorrectly caught as novel defects.

The embodiments described above can be used to monitor classifiers in, for example, electron beam based defect review, and other processes performed in production. For example, for novel defect detection inline, for every nth production lot run, the rejected bin data for that lot may be combined with previous n−1 rejected bin data. The novelty detection steps described herein may be performed using the combined data and the novel class for that lot may be reported inline. In addition, as described further herein, the embodiments can act as a safeguard against performance degradation. The embodiments can also generate an alarm indicating a process excursion, which may be of critical interest to the user. For example, the embodiments described herein provide a general approach that can be used to detect clusters of novel classes in production and is applicable across electron beam based and light based use cases. Without a mechanism in place to detect novel classes in production and monitoring of classifiers, current ADC solutions would not be adopted in production. Thus, novel defect detection is a critical ingredient in the overall ADC solution for production.

The embodiments described herein may also be configured for estimating a drop in defect bin purity due to novel class appearance on a layer. For example, once a rejected bin has been classified by a user, the rejected bin may be added to the training data as described further herein and used to re-train the classifier, which may be performed as described further herein. The defects previously classified by that classifier may then be re-run through the re-trained classifier to get another set of classifications for that data. The defects classified to the novel class (i.e., the class of the rejected defects that has been manually assigned a novel class by the user) in this additional run may then be used to estimate purity drops in the original classifier.

In addition, the embodiments can be directly used for continuous defect discovery. For example, the embodiments described herein may provide a critical ingredient of the continuous discovery use case where the goal is to provide customers with a relatively small sample population of potential new defect types on production wafers whenever it is applicable. Once an inspection or defect review recipe is in production, users monitor the recipe primarily for nuisance rate and excursions. Random sampling may be performed on production lots, the sample may be reviewed and classified to assess the nuisance rate on production wafers, and users may also get to see a pareto of defects from random sampling. The current ADC solution is unable to report novel classes as part of the pareto and thus there is a need to make users aware of potential new defect types on the wafer using a novelty detection method.

The embodiments described herein may also be configured for using sequential classifiers for classifier performance robustness. For example, the embodiments described herein provide an improved method for classifier creation by giving higher priority to a select list of stable attributes to improve the consistency in performance of a classifier when ported across different tools and stability of performance irrespective of tool parameter state.

In currently used random forest based ADC methods, ranking the attributes for classifier creation has been performed by considering only the sole criteria of separation based attributes and has not taken into account the stability of the attributes with tool drift. Such ranking of the attributes may be performed internally by the random forest method while building the decision trees based on the amount of separation between different types of defects given by each attribute. Thus, currently no method exists to perform the functions described further herein. In addition, the currently used methods for classifier creation do not have any method of dealing with defect types with substantially few examples. In this manner, defect types with substantially few examples can end up interfering with the major defect bins, which can decrease their purity below performance specifications.

The currently used methods have, therefore, a number of disadvantages. For example, in the currently used methods for classifier creation, in the cases where separation is achieved using both stable and unstable attributes, in some cases, unstable attributes were given higher ranking over stable attributes. As a result, the classifier created in such a manner can have inconsistent performance when ported across different tools and also due to variation in tool parameters. In particular, the currently used ADC methods are unable to deal with tool/imaging drift. In another example, the currently used methods do not have any method of introducing prior information about defect classes with substantially few examples. This information about a defect type and its properties is generally provided by users and can be helpful in pruning out these defect types. In an additional example, the currently used approaches put substantially severe bounds on tool-to-tool matching for multi-tool classifier setup, and if two tools were out of specification, their data could not be used to setup a common classifier.

The embodiments described herein provide a feasible solution for stable classifier performance that is robust to tool drift and for stable performance when a classifier is ported across different tools. Even under stable tool conditions on some electron beam based defect review tools, intensity based defect attributes showed relatively high variation in attributes across different tools. For example, for intensity based P1 attributes (energy density P1 and polarity P1, where P1 indicates image features calculated on a top perspective image of the specimen, which may be generated using one or more algorithms and post-processing by giving different weights to different channels of the detector), the variation in attributes for the same defect type across different tools may be close to ~50% and for intensity based P0 attributes (Intensity StdMix0, where P0 indicates image features calculated from the Mix0 perspective, which is the perspective generated by adding all channels with equal weights and without any post-processing, and where StdMix0 is a defect attribute that is calculated as the standard deviation of the defect pixels in the image calculated on the Mix0 perspective), it was found to be close to ~40%. However, variation in attributes that are topography based is relatively low. For example, a mean height attribute showed less than 15% variation across different tools. Owing to relatively high variation of intensity based attributes across different tools, using such attributes during classifier creation was found to make the classifier performance unstable.

In one embodiment, the created defect classifier includes at least a first defect classifier and a second defect classifier arranged in a sequence such that only the defects classified by the first defect classifier with a confidence below another confidence threshold are sent to the second defect classifier, the first defect classifier is configured to use only a first portion of defect attributes determined by the one or more computer subsystems for the defects to separate the defects into one or more first classes, and the first portion of the defect attributes are substantially stable to drift in one or more parameters of the output acquisition subsystem. The embodiments described herein, therefore, provide methods of setting up classifiers in a sequence, one based on just the stable attributes followed by another based on all attributes (or at least some relatively unstable attributes) to provide classifiers stable to tool drift. In addition, the embodiments provide classifiers that have stable classifier performance on an electron beam based defect review tool (and other tools described herein), that are robust to tool drift, and that may include pruning classes with substantially few defect examples to improve the purity of the results produced by the classifier.

In one such embodiment, the first portion of the defect attributes includes one or more topography based attributes. In another such embodiment, the first portion of the defect attributes includes one or more shape based attributes. In an additional such embodiment, the first portion of the defect attributes does not include intensity based attributes. For example, it has been determined that topography based attributes show relatively stable performance across different tools. Therefore, it was found that creating a sequential classifier making use of only relatively stable attributes (e.g., topography based and shape based attributes) in the cases where they can provide a relatively good separation between defect classes and using other relatively unstable attributes only in the cases where the stable attributes could not provide good separation between defect classes can lead to consistent classifier performance. Thus, the attributes can be separated based on their susceptibility to change due to tool parameters. In this manner, the highest priority can be given to relatively stable attributes to build the first classifier.

In another such embodiment, the second defect classifier is configured to use a second portion of the defect attributes to separate the defects into one or more second classes, and the second portion of the defect attributes are less stable to the drift than the first portion of the defect attributes. For example, when the attributes are separated based on their susceptibility to change due to tool parameters, higher priority can be given to relatively stable attributes to build the first classifier and the second classifier can be built with all attributes, not just the substantially stable defect attributes. For example, in some such embodiments, the second portion of the defect attributes includes one or more intensity based attributes. In addition, the second portion of the defect attributes may include all defect attributes available for classification. As such, a classifier based on substantially stable defect attributes may be followed sequentially by a classifier based on all attributes. In this manner, only the defects classified with relatively low confidence by the first classifier can be sent to the second classifier thereby leading to substantially stable classifier performance. Therefore, the embodiments described herein provide classifier performance that is substantially stable to tool drift.

In a further such embodiment, the first portion of the defect attributes are substantially stable to differences between the one or more parameters of the output acquisition subsystem and one or more parameters of another output acquisition subsystem. In one such embodiment, the one or more computer subsystems are configured for classifying defects detected based on output generated by the other output acquisition subsystem with the created defect classifier. Therefore, the embodiments described herein provide substantially stable classifier performance after porting the classifier from one tool to another. For example, the sequential classifier can be ported to another tool with different tool/imaging conditions to provide robust performance on the other tool. The robust performance on multiple tools is provided by the fact that the set of defects classified by the first sequential classifier are essentially guaranteed to be classified on all tools independent of tool conditions. Additionally, only the first sequential classifier, which is based on stable attributes such as topographical and shape attributes, may be ported to the other tool until sufficient data can be collected to validate the performance of the second sequential classifier on the other tool. In this manner, the embodiments described herein may be configured for porting the sequential classifier or just the first classifier from one tool to another.

In a further such embodiment, the training set of defects used to create the defect classifier also includes defects detected based on output generated by another output acquisition subsystem, and the output acquisition subsystem and the other output acquisition subsystem are not matched to each other when the output was generated by the output acquisition subsystem and the other output acquisition subsystem. For example, currently used ADC techniques do not use data from multiple tools to build a classifier if each of the multiple tools is not within specifications. The embodiments described herein, however, provide a way to use this data to setup multi-tool classifiers, even if one or more of the tools are out of specification, and thus time to setup multi-tool classifiers is significantly reduced. More specifically, if topographical attributes are more immune to tool drift, this data could be used to setup the first sequential classifier, a classifier built on just relatively stable attributes such as topographical and/or shape attributes. Therefore, the embodiments described herein can use multi-tool data to setup sequential classifiers even if the tools are not matched and/or are out of specification.

In another such embodiment, the created defect classifier includes a third defect classifier arranged in the sequence such that results of applying at least the first and second defect classifiers are input to the third defect classifier, and the third defect classifier is a manual decision tree. In contrast to the embodiments described herein, currently used random forest based ADC classifiers are unable to separate classes with substantially few defects from the major classes due to lack of examples. However, a manual cutline based approach may be used to separate out such defect classes based on prior knowledge from the user. Therefore, the embodiments described herein provide classifier performance that is stable on layers with a relatively large number of defect types with relatively few examples.

In one such example, the third sequential classifier may be a set of decisions based on some attributes and prior knowledge. For example, there may be two defects of a class in a training set, but two defects is not enough to train using machine learning techniques. However, a user may indicate that the defects have a significant height, e.g., higher than other defect types. Then, a decision tree based on height attributes can be added to filter out defects with relatively large height. This decision would constitute the third classifier. More than one decision can be added based on such prior knowledge. All these decisions, similar to a decision tree, may then constitute the third classifier.

In this manner, the defect classifiers described herein may be 3-step sequential classifiers, which are robust to tool drift and defect classes with small numbers. As described further above, the first classifier may be a random forest classifier built with just the relatively stable ADC attributes, i.e., the set of attributes known to be stable to imaging tool variations. The second classifier may be a random forest classifier built with all ADC attributes. The third classifier may be a manual decision tree based on prior knowledge where engineers set manual cutlines to filter out relatively small defect classes that are interfering with existing classes. In this manner, a manual decision tree may be used to prune out defects with substantially few examples based on prior knowledge.

Figure 6:
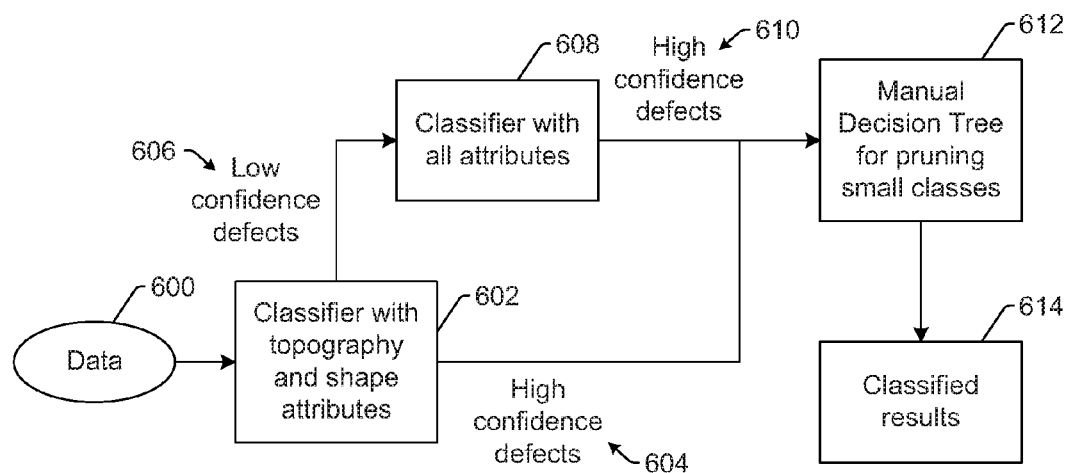
FIG. 6 is a flow diagram illustrating one embodiment of steps that may be performed by one or more computer subsystem embodiments described herein for defect classification with a sequence of defect classifiers.

One such embodiment is shown in FIG. 6. As shown in this figure, data 600 may be input to the classifier by being input to first classifier 602 that is configured as a classifier based on topography and/or shape attributes. In addition, first classifier 602 may be built on just topographical and shape-based attributes. The defects that are well separated using just these attributes would get well separated by this classifier. In other words, such defects may include high confidence defects 604. Since these attributes are substantially stable with tool drift, these defects would always get correctly classified with high confidence even after tool drift. The rest of the defects, i.e., low confidence defects 606 or defects that are not classified by the first classifier with relatively high confidence, may be sent to the next sequential classifier, which may be a random forest classifier based on all available defect attributes. For example, as shown in FIG. 6, the low confidence defects may be sent to second classifier 608 that is a classifier based on all attributes. Classification performed by this classifier may generate results including high confidence defects 610, which may be combined with high confidence defects 604, and sent to third classifier 612, which is a manual decision tree for pruning relatively small classes. For example, the third sequential classifier may be a manual decision tree that is built with each classifier bin as a root node to prune out defects with substantially few examples. In one such example, if line bridging is getting classified as bridging, a manual decision tree may be built on the ADC bin for bridging, i.e., the set of defects classified as bridging in the first and second sequential classifiers, to prune out line bridging.

The defect classifier embodiments described above, therefore, provide a number of advantages over currently used defect classifiers. For example, the embodiments described herein provide a method of building a classifier that is robust to tool drift or variation in imaging conditions over time. Some studies performed by the inventors have shown that almost 90% of the defects can be separated out using just topographical and shape based attributes. Thus, with the sequential classifier embodiments described herein, 90% of the performance will be guaranteed even if the tool drifts.

Therefore, the embodiments described herein can be used to build classifiers that are more resilient to changing conditions.

In another example, the embodiments provide a method of dealing with classes with substantially few defects that are known to degrade classifier performance. In contrast, the currently used ADC methods are unable to maintain performance on layers with substantially large numbers of minority defect classes with substantially few example defects, which is a common use case across fabs and can severely hamper ADC performance.

In an additional example, the embodiments provide a method for porting classifiers across tools, which might have varying tool/imaging conditions. In contrast, currently used ADC methods are severely affected by tool drift and do not have any solutions for efficient porting of classifiers. Thus, currently, severe constraints are placed on system stability that is hard to meet without constant recalibrations. For example, in currently used ADC methods, all defect types are susceptible to tool drift, but in the sequential classifiers described herein, only the defects that the topography and shape based attributes are unable to classify are susceptible to tool drift. If, after porting, the classifier is found to be not working, in currently used ADC methods, the full classifier is re-trained, while for the sequential classifiers described herein only the second classifier may be re-trained. Therefore, the embodiments described herein enable efficient tool-to-tool porting of classifiers and improve classifier performance by pruning out defect classes with relatively few defects.

In a further example, the embodiments provide a method for using multi-tool data for classifier setup even if the tool imaging conditions are substantially different. In this manner, the embodiments described herein provide relatively easy multi-tool setup of classifiers without placing strict bounds on tool matching. The embodiments described herein may be therefore critical to the success of ADC methods. In this manner, ADC work may involve classifier setup from multiple tools, which though initially matched, drift over time. It is, therefore, critical to ensure that multi-tool classifiers can be setup such that they are able to deal with drifting tool conditions. The sequential classifiers would provide a more robust and reliable way to setup classifiers that are invariant to tool drift and significantly relax the bounds on tool-to-tool matching.

Another embodiment relates to a computer-implemented method for classifying defects on a specimen with an adaptive automatic defect classifier. The method includes steps for each of the functions of the computer subsystem(s) described above.

Each of the steps of the method may be performed as described further herein. The method may also include any other step(s) that can be performed by the output acquisition subsystem and/or computer subsystem(s) or system(s) described herein. The steps of the method are performed by one or more computer systems, which may be configured according to any of the embodiments described herein. In addition, the method described above may be performed by any of the system embodiments described herein.

Figure 7:
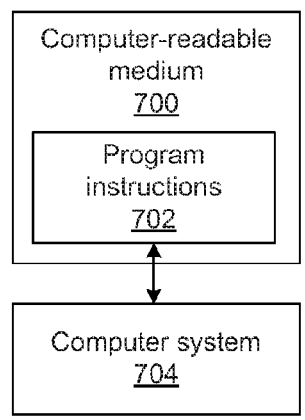
FIG. 7 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for classifying defects on a specimen with an adaptive automatic defect classifier. One such embodiment is shown in FIG. 7. In particular, as shown in FIG. 7, non-transitory computer-readable medium 700 includes program instructions 702 executable on computer system 704. The computer-implemented method may include any step(s) of any method(s) described herein.

Program instructions 702 implementing methods such as those described herein may be stored on computer-readable medium 700. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 704 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Further modifications and alternative embodiments of various aspects of the invention will be apparent to those skilled in the art in view of this description. For example, methods and systems for classifying defects on a specimen with an adaptive automatic defect classifier are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to classify defects on a specimen with an adaptive automatic defect classifier, comprising:

an output acquisition subsystem comprising at least an energy source and a detector, wherein the energy source is configured to generate energy that is directed to a specimen, and wherein the detector is configured to detect energy from the specimen and to generate output responsive to the detected energy; and one or more computer subsystems configured for:

detecting defects on the specimen based on the output generated by the detector to thereby generate first lot results;

separating the defects into different groups using a clustering method;

receiving a classification for each of the different groups from a user;

creating a defect classifier based on the received classifications and a training set of defects comprising all the defects in the first lot results;

determining a robustness score for the created defect classifier by perturbing the training set in one or more attributes of the defects used by the created defect classifier for classifying the defects and determining an amount of perturbation the created defect classifier can withstand before performance of the created defect classifier drops below a predetermined level;

determining one or more control settings for one or more parameters of the output acquisition subsystem based on the robustness score;

detecting additional defects on another specimen of the same type as the specimen based on additional output generated by the detector for the other specimen to thereby generate additional lot results;

combining the first and additional lot results to create cumulative lot results;

classifying the defects in the cumulative lot results by applying the created defect classifier to the defects in the cumulative lot results;

determining if any of the defects in the additional lot results have a confidence value that is below a confidence threshold;

when one or more of the defects in the additional lot results have a confidence value that is below the confidence threshold, receiving one or more classifications for the one or more defects from a user and modifying the training set to include the one or more defects and the one or more classifications;

modifying the defect classifier based on the modified training set;

classifying defects in the cumulative lot results with the modified defect classifier; and when all of the defects in the cumulative lot results are classified by the user or none of the defects in the additional lot results have a confidence value that is below the confidence threshold, finishing adaptive classifier creation.

2. The system of claim 1, wherein creating the defect classifier is performed with automatic confidence threshold, and wherein creating the defect classifier with the automatic confidence threshold comprises, for each defect type, increasing a confidence threshold from a minimum value until reaching a purity target.

3. The system of claim 1, wherein the created defect classifier is a random forest type defect classifier.

4. The system of claim 1, wherein the created defect classifier is a supported vector machine type defect classifier.

5. The system of claim 1, wherein the one or more computer subsystems are further configured for determining a data redundancy score by:

a) for a first class of multiple classes of defects, selecting a portion of the defects in the first class using a clustering method and adding the selected portion of the defects to a training set for the first class;

b) creating an automated classifier with the training set for the first class and training sets of other classes of the multiple classes;

c) classifying a portion of the defects in the first class that were not selected in step a) with the automated classifier;

d) if any defects in the first class are classified below a predefined confidence threshold by the automated classifier, adding a predetermined number of the defects in the first class to the training set for the first class and repeating steps a) to c); and e) if none of the defects in the first class are classified below the predefined confidence threshold by the automated classifier, calculating the data redundancy score as equal to 1−(size of the training set fir the first class) divided by (size of the first class).

6. The system of claim 1, wherein the one or more computer subsystems are further configured for monitoring a size of a bin of unclassified defects in results produced by the created defect classifier and the modified defect classifier and generating an alarm when the size of the bin is greater than a predetermined size, and wherein the alarm indicates that calibration of the one or more parameters of the output acquisition subsystem is necessary.

7. The system of claim 1, wherein the one or more computer subsystems are further configured for monitoring a confidence histogram of each defect bin in results produced by the created defect classifier and the modified defect classifier and generating an alarm when the confidence histogram has one or more predetermined characteristics, and wherein the alarm indicates that calibration of the one or more parameters of the output acquisition subsystem is necessary.

8. The system of claim 1, wherein the one or more computer subsystems are further configured for:

appending defects in a bin of unclassified defects produced by e created defect classifier or the modified defect classifier to the training set or the modified training set, respectively, thereby creating an additional training set;

training another classifier on the additional training set, wherein the other classifier classifies two or more of the defects in the additional training set to an additional bin of unclassified defects;

separating the defects in the additional bin based on confidence of the other classifier assigned to each of the defects in the additional bin such that the defects having a confidence above another confidence threshold are assigned to a first bin and defects having a confidence below the other confidence threshold are assigned to a second bin, wherein the first bin is a preliminary novel bin;

appending the preliminary novel bin to the training set or the modified training set, respectively, thereby creating a further training set;

training an additional classifier on the further training set;

classifying the defects assigned to the second bin with the additional classifier to thereby, separate the defects assigned to the second bin into defects assigned to the second bin with a confidence above an additional confidence threshold and defects assigned to the second bin with a confidence below the additional confidence threshold; and adding the defects assigned to the second bin with the confidence above the additional confidence threshold to the preliminary novel bin to thereby create a final novel bin.

9. The system of claim 8, wherein the one or more computer subsystems are further configured for:

appending the defects in the final novel bin to the training set or the modified training set, respectively, thereby creating another further training set;

re-training the created defect classifier or the modified defect classifier, respectively, based on the other further training set such that the re-trained defect classifier produces an additional novel bin corresponding to the final novel bin; and classifying the defects in one or more bins other than the bin of unclassified defects produced by the created defect classifier or the modified defect classifier, respectively, with the re-trained defect classifier such that the defects in the one or more bins that are novel defects are moved from the one or more bins to the additional novel bin.

10. The system of claim 8, wherein the one or more computer subsystems are further configured for comparing a size of the final novel bin to a threshold and triggering re-training of the created defect classifier or the modified defect classifier, respectively, when the size of the final novel bin is above the threshold.

11. The system of claim 1, wherein the created defect classifier comprises at least a first defect classifier and a second defect classifier arranged in a sequence such that only the defects classified by the first defect classifier with a confidence below another confidence threshold are sent to the second defect classifier, and wherein the first defect classifier is configured to use only a first portion of defect attributes determined by the one or more computer subsystems for the defects to separate the defects into one or more first classes.

12. The system of claim 11, wherein the first portion of the defect attributes comprise one or more topography based attributes.

13. The system of claim 11, wherein the first portion of the defect attributes comprise one or more shape based attributes.

14. The system of claim 11, wherein the first portion of the defect attributes does not comprise intensity based attributes.

15. The system of claim 11, wherein the second defect classifier is configured to use a second portion of the defect attributes to separate the defects into one or more second classes.

16. The system of claim 15, wherein the second portion of the defect attributes comprise one or more intensity based attributes.

17. The system of claim 11, wherein the one or more computer subsystems are further configured for classifying defects detected based on output generated by another output acquisition subsystem with the created defect classifier.

18. The system of claim 11, wherein the training set of defects used to create the defect classifier further comprises defects detected based on output generated by another output acquisition subsystem, and wherein the output acquisition subsystem and the other output acquisition subsystem are not, matched to each other when the output was generated by the output acquisition subsystem and the other Output acquisition subsystem.

19. The system of claim 11, wherein the created defect classifier further comprises a third defect classifier arranged in the sequence such that results of applying at least the first and second detect classifiers are input to the third detect classifier, and wherein the third defect classifier comprises a manual decision tree.

20. The system of claim 1, wherein the specimen comprises a wafer.

21. The system of claim 1, wherein the energy directed to the specimen comprises light, and wherein the energy detected from the specimen comprises light.

22. The system of claim 1, wherein the energy directed to the specimen comprises electrons, and wherein the energy detected from the specimen comprises electrons.

23. A non-transitory computer-readable medium, storing program instructions executable on a computer system for performing a computer-implemented method for classifying defects on a specimen with an adaptive automatic defect classifier, wherein the computer-implemented method comprises:
  detecting defects on the specimen based on output generated by a detector of an output acquisition subsystem to thereby generate first lot results, wherein the output acquisition subsystem comprises at least an energy source and the detector, wherein the energy source is configured to generate energy that is directed to a specimen, and wherein the detector is configured to detect energy from the specimen and to generate the output responsive to the detected energy;
  separating the defects into different groups using a clustering method;
  receiving a classification for each of the different groups from a user;
  creating a defect classifier based on the received classifications and a training set of defects comprising all the defects in the first lot results;
  determining a robustness score for the created defect classifier by perturbing the training set in one or more attributes of the defects used by the created defect classifier for classifying the defects and determining an amount of perturbation the created defect classifier can withstand before performance of the created defect classifier drops below a predetermined level;
  determining one or more control settings for one or more parameters of the output acquisition subsystem based on the robustness score;
  detecting additional defects on another specimen of the same type as the specimen based on additional output generated by the detector for the other specimen to thereby generate additional lot results;
  combining the first and additional lot results to create cumulative lot results;
  classifying the defects in the cumulative lot results by applying the created defect classifier to the defects in the cumulative lot results;
  determining if any of the defects in the additional lot results have a confidence value that is below a confidence threshold;
  when one or more of the defects in the additional lot results have a confidence value that is below the confidence threshold, receiving one or more classifications for the one or more defects from a user and modifying the training set to include the one or more detects and the one or more classifications;
  modifying the defect classifier based on the modified training set;
  classifying defects in the cumulative lot results with the modified defect classifier; and
  when all of the defects in the cumulative lot results are unclassified by the user or none of the defects in the additional lot results have a confidence value that is below the confidence threshold, finishing adaptive classifier creation.

24. A computer-implemented method for classifying defects on a specimen with an adaptive automatic defect classifier, comprising:
  detecting defects on the specimen based on output generated by a detector of an output acquisition subsystem to thereby generate first lot results, wherein the output acquisition subsystem comprises at least an energy source and the detector, wherein the energy source is configured to generate energy that is directed to a specimen, and wherein the detector is configured to detect energy from the specimen and to generate the output responsive to the detected energy;

separating the defects into different groups using a clustering method;

receiving a classification each of the different groups from a user;

creating a defect classifier based on the received classifications and a training set of defects comprising all the defects in the first lot results;

determining a robustness score for the created defect classifier by perturbing the training set in one or more attributes of the defects used by the created defect classifier for classifying the defects and determining an amount of perturbation the created defect classifier can withstand before performance of the created defect classifier drops below a predetermined level;

determining one or more control settings for one or more parameters of the output acquisition subsystem based on the robustness score;

detecting additional defects on another specimen of the same type as the specimen based on additional output generated by the detector for the other specimen to thereby generate additional lot results;

combining the first and additional lot results to create cumulative lot results;

classifying the defects in the cumulative lot results by applying the created defect classifier to the defects in the cumulative lot results;

determining if any of the defects in the additional lot results have a confidence value that is below a confidence threshold;

when one or more of the defects in the additional lot results have a confidence value that is below the confidence threshold, receiving one or more classifications for the one or more defects from a user and modifying the training set to include the one or more defects and the one or more classifications;

modifying the defect classifier based on the modified training set;

classifying defects in the cumulative lot results with the modified defect classifier; and when all of the defects in the cumulative lot results are unclassified by the user or none of the defects in the additional lot results have a confidence value that is below the confidence threshold, finishing adaptive classifier creation, wherein steps of the method are performed by one or more computer systems.

* * * * *